US008054159B2

(12) United States Patent
Hyoung et al.

(10) Patent No.: US 8,054,159 B2
(45) Date of Patent: Nov. 8, 2011

(54) COMMUNICATION APPARATUS HAVING HUMAN BODY CONTACT SENSING FUNCTION AND METHOD THEREOF

(75) Inventors: Chang-Hee Hyoung, Daejeon (KR);
Jin-Bong Sung, Daejeon (KR);
Sung-Weon Kang, Daejeon (KR);
Jung-Hwan Hwang, Daejeon (KR);
Duck-Gun Park, Daejeon (KR);
Jin-Kyung Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 524 days.

(21) Appl. No.: 12/096,365

(22) PCT Filed: Dec. 6, 2006

(86) PCT No.: PCT/KR2006/005247
§ 371 (c)(1),
(2), (4) Date: Jun. 5, 2008

(87) PCT Pub. No.: WO2007/066979
PCT Pub. Date: Jun. 14, 2007

(65) Prior Publication Data
US 2008/0284607 A1    Nov. 20, 2008

(30) Foreign Application Priority Data
Dec. 8, 2005  (KR) .................. 10-2005-0120053
Aug. 9, 2006  (KR) .................. 10-2006-0075295

(51) Int. Cl.
*G06F 7/04*    (2006.01)
(52) U.S. Cl. .... 340/5.64; 340/5.1; 340/5.65; 340/10.34; 340/573.1; 455/41.1
(58) Field of Classification Search .................. 340/5.1, 340/5.2, 5.65, 5.64, 10.51, 10.34, 573.1, 340/825.72
See application file for complete search history.

(56) References Cited

U.S. PATENT DOCUMENTS
4,591,854 A    5/1986    Robinson
(Continued)

FOREIGN PATENT DOCUMENTS
JP    2002-009710    1/2002
(Continued)

OTHER PUBLICATIONS

Korean Intellectual Property Office, International Search Report for International Application No. PCT/KR2006/005247, 3 pages (Date completed: Feb. 27, 2007).

(Continued)

*Primary Examiner* — Brent Swarthout

(57) ABSTRACT

Provided is a communication apparatus having a human body contact sensing function and a method thereof. The communication apparatus includes: an electrode that comes in contact with the human body; a contact sensor that is connected to the electrode, and instructs the central processing unit to perform an initial operation if contact with the human body is sensed; and a data processing unit that receives a control signal from the central processing unit so as to select whether to transmit or receive data, and performs a transmitting or receiving operation according to the control signal. Accordingly, in order to reduce power consumption when in a stand-by state before human body contact is made in a communication apparatus using a human body as a communication medium, a human body contact sensor is included so as to minimize power consumption of a micro processing unit and a transmitter/receiver circuit until contact occurs. Therefore, since power consumption is minimized when in a stand-by mode by using a contact sensor having significantly low power consumption, there is an advantage in that a stand-by time of a portable device is extended.

11 Claims, 9 Drawing Sheets

U.S. PATENT DOCUMENTS

| | | | |
|---|---|---|---|
| 5,796,827 A | | 8/1998 | Coppersmith et al. |
| 5,811,897 A | * | 9/1998 | Spaude et al. ............... 307/149 |
| 6,223,018 B1 | * | 4/2001 | Fukumoto et al. ........... 455/41.1 |
| 6,771,161 B1 | * | 8/2004 | Doi et al. ...................... 340/5.64 |
| 6,864,780 B2 | * | 3/2005 | Doi et al. ...................... 340/5.64 |
| 2002/0030585 A1 | * | 3/2002 | Doi et al. ...................... 340/5.64 |
| 2004/0152440 A1 | | 8/2004 | Yoda et al. |
| 2005/0017841 A1 | * | 1/2005 | Doi et al. ...................... 340/5.65 |
| 2006/0153109 A1 | | 7/2006 | Fukumoto et al. |
| 2008/0284607 A1 | | 11/2008 | Hyoung et al. |
| 2010/0045446 A1 | * | 2/2010 | Hyun et al. ................ 340/10.51 |

FOREIGN PATENT DOCUMENTS

| | | |
|---|---|---|
| JP | 2002-152145 A | 5/2002 |
| JP | 2005-004383 A | 1/2005 |
| JP | 2005-086685 A | 3/2005 |
| JP | 2005-159618 A | 6/2005 |
| JP | 2006-318485 A | 11/2006 |
| KR | 1020030018523 A | 3/2003 |
| KR | 1020070061251 A | 6/2007 |
| KR | 1020070090412 A | 9/2007 |

OTHER PUBLICATIONS

Shinagawa et al., "A Near-Field-Sensing Transceiver for Intra-Body Communication Based on the Electro-Optic Effect" IMTC 2003, pp. 296-301 (May 2003).

Eric Wade et al., "Electrostatic Analysis and Design of a Cable-Free Body Area Network of Sensor Nodes Using 2D Communication over Conductive Fabric Sheets", Intelligent Robots and Systems, 2005 (IROS 2005), Aug. 2, 2005, pp. 3642-3647.

Nobuyuki Matsushita et al., "Wearable Key: Device for Personalizing nearby Environment", Proceedings of the Fourth International Symposium on Wearable Computers, Oct. 16, 2000, pp. 119-126, IEEE.

\* cited by examiner

COMMUNICATION APPARATUS HAVING HUMAN BODY CONTACT SENSING FUNCTION AND METHOD THEREOF

CROSS REFERENCE TO RELATED APPLICATIONS

This application is a US National Stage of International Patent Application No. PCT/KR2006/005247, filed Dec. 6, 2006, which in turn claims the benefit of Korean Patent Application No. 10-2005-0120053, filed Dec. 8, 2005 and Korean Patent Application 10-2006-0075295, filed Aug. 9, 2006, the disclosures of all three applications are incorporated herein by reference.

TECHNICAL FIELD

The present invention relates to a communication apparatus that allows a controller and a transmitter/receiver module for human body communication to enter a normal operation state from a stand-by mode by sensing contact or approach of human body by using a method of transmitting a signal between devices which are mounted on or placed near the human body as a communication medium, and a method thereof.

BACKGROUND ART

A conventional system for human body communication, in which devices mounted on or placed near a human body communicate with one another through the human body as a communication medium, allows a communication channel to be formed when in contact with the human body. However, it is uncertain when a device embedded with a human body communication module will come in contact with the human body, and thus a signal needs to be periodically checked so as to find out whether a communication channel has been formed between corresponding devices. In this case, even if there is no contact with the human body, the device itself cannot recognize whether there is contact with the human body. Therefore, not only a receiving-end circuit that converts a weak signal received through the human body into a digital signal that can be processed by a micro-controller but also a micro-controller that performs a control operation has to be constantly or periodically in a wake-up state to reduce power consumption.

When a transmitter has data to be sent, even if a human body communication micro-controller initially operates after data is output to an external control signal or a designated memory area, a transmitter circuit that converts the digital signal received from the micro-controller into a signal to be output to the human body has to be operated in a normal state until contact with the human body has been made. That is, in order to check whether a channel is formed, the transmitter circuit has to operate even if there is no contact with the human body, which leads to unnecessary power consumption.

As described above, power is unnecessarily consumed because a transmitter/receiver circuit and a micro-controller for controlling the transmitter/receiver circuit have to constantly or periodically be in the normal state so as to determine whether a channel has been formed in transmitting and receiving processes even if there is no contact with the human body.

DISCLOSURE OF INVENTION

Technical Problem

The present invention provides an apparatus that has a reduced unnecessary power consumption of a transmitter circuit, a receiver circuit, and a micro-controller that controls the transmitter and receiver circuits, wherein the power consumption may be reduced before contact with a human body is made when communication is achieved through the human body as a communication medium, and a method thereof.

Technical Solution

According to an aspect of the present invention, there is provided a communication apparatus having a human body contact sensing function wherein the communication apparatus performs communication in contact with a central processing unit and a human body, the communication apparatus comprising: an electrode that comes in contact with the human body; a contact sensor that is connected to the electrode, and instructs the central processing unit to perform an initial operation if contact with the human body is sensed; and a data processing unit that receives a control signal from the central processing unit so as to select whether to transmit or receive data, and performs a transmitting or receiving operation according to the control signal.

In the aforementioned aspect of the present invention, the contact sensor may instruct the central processing unit to perform the initial operation by sensing direct contact between the human body and the electrode or by sensing approach of the human body.

In addition, the data processing unit may perform transmitting and receiving of the data by using a time-division method.

In addition, the data processing unit may further perform a process by using a continuous frequency modulation method in which the same carrier frequency is used when the data is transmitted and received.

In addition, the data processing unit may further perform transmitting and receiving of the data by using a continuous frequency modulation method in which a transmission carrier frequency is different from a reception carrier frequency.

According to another aspect of the present invention, there is provided a communication apparatus having a human body contact sensing function wherein the communication apparatus performs communication in contact with a central processing unit and a human body, the communication apparatus comprising: an electrode that comes in contact with a human body; a sensor that converts an electric field input through the electrode into an electric signal; a data processing unit that restores the electric signal into original data to be transmitted to an external device, and converts data received from the external device to output the received data to the electrode; and a contact sensor that generates and outputs a sensing signal used to detect whether contact is made with the human body and indicates the result of detection so that the external device can recognize the result, and that comprises a multi-channel sensor if the electrode is provided in plural.

In the aforementioned aspect of the present invention, the external device may perform an initial operation in response to the sensing signal.

According to another aspect of the present invention, there is provided a communication method having a human body contact sensing function wherein the communication method performs communication in contact with a central processing unit and a human body, the communication method comprising: determining whether contact is made with the human body; instructing the central processing unit to perform an initial operation if the determination result is positive; and transmitting or receiving data in response to a control signal from/to the central processing unit which has performed the initial operation.

ADVANTAGEOUS EFFECTS

In a communication apparatus having a human body contact sensing function and a method thereof, in order to reduce power consumption when in a stand-by state before human body contact is made with the communication apparatus which uses a human body as a communication medium, a human body contact sensor is inserted so as to minimize power consumption of a micro processing unit and a transmitter/receiver circuit until contact occurs. Therefore, since power consumption is minimized when in a stand-by mode by using a contact sensor having significantly low power consumption, there is an advantage in that a stand-by time of a portable device is extended.

That is, since a contact sensing function is additionally provided to determine whether a human body comes in contact with an electrode for transmitting and receiving a signal, it is possible to reduce unnecessary power consumption which may be produced until human body contact is made.

DESCRIPTION OF DRAWINGS

The features and advantages of the present invention will become more apparent by describing in detail exemplary embodiments thereof with reference to the attached drawings in which.

MODE FOR INVENTION

Hereinafter, exemplary embodiments of the present invention will be described with reference to the accompanying drawings.

Figure 1:
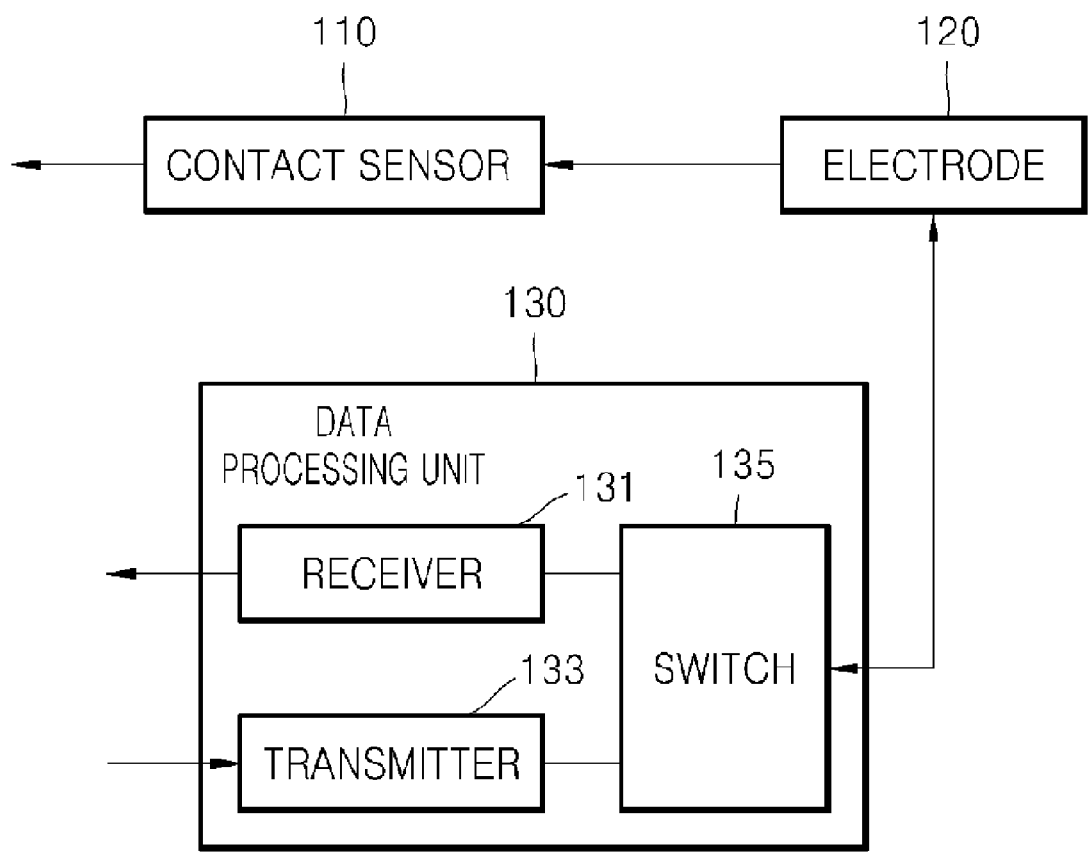
FIG. 1 is a block diagram illustrating a configuration of a communication apparatus having a human body contact sensing function according to an embodiment of the present invention.
Figure 12:
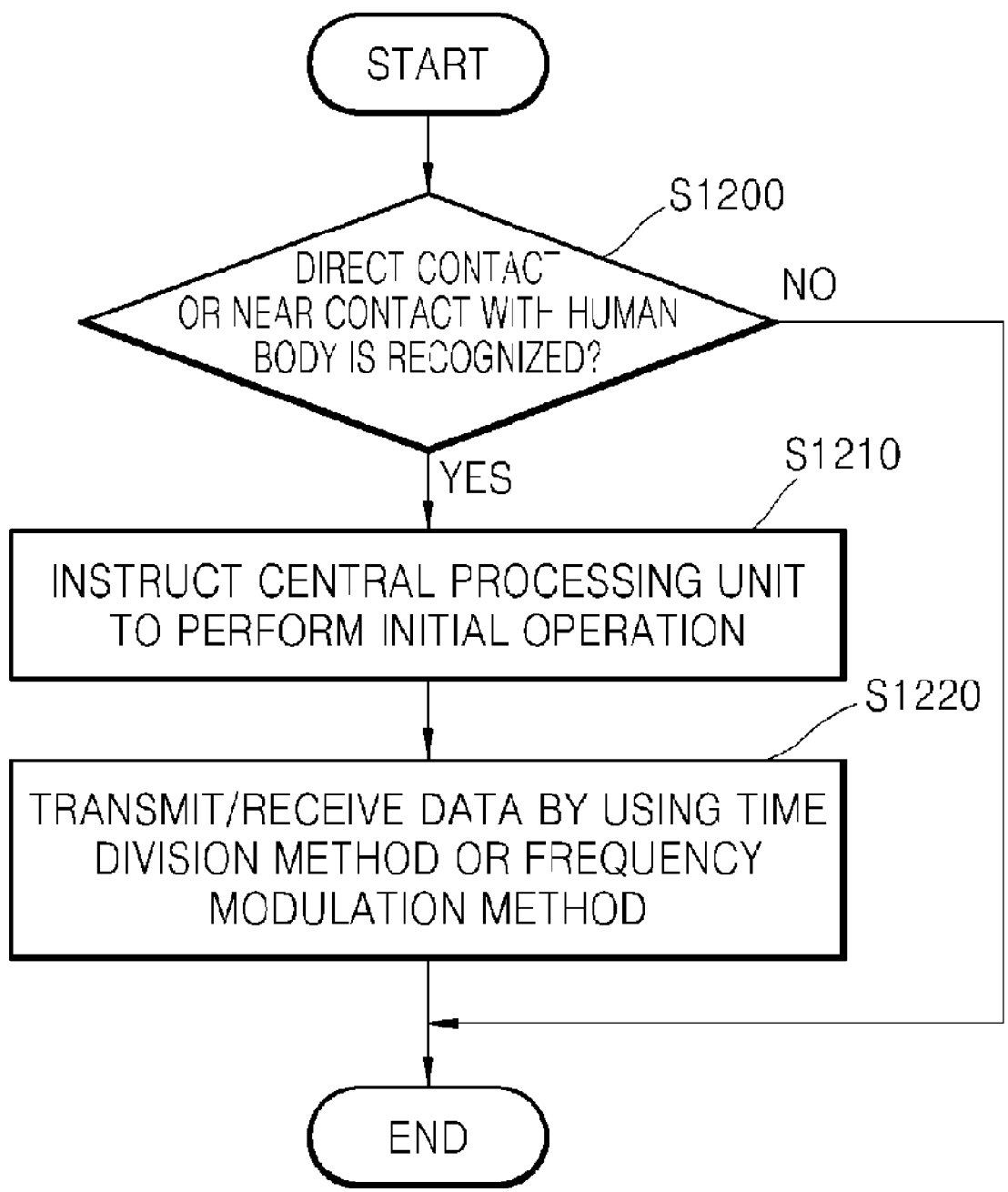
FIG. 12 is a flowchart illustrating a communication method of sensing human body contact according to an embodiment of the present invention.

FIG. 1 is a block diagram illustrating a configuration of a communication apparatus having a human body contact sensing function according to an embodiment of the present invention. FIG. 12 is a flowchart illustrating a communication method of sensing human body contact according to an embodiment of the present invention. According to an embodiment of the present invention, a contact sensor is provided to wake up a micro-controller by connecting a sensor having a contact sensing function to an electrode for transmitting/receiving a signal with a human body, thereby detecting contact or approach of the human body. Since a human body communication module operates by using human body contact, power is not consumed as a micro-controller and transmitter/receiver circuits operate in the absence of human body contact. As a result, a portable device using the human communication module can have an improved stand-by time.

A contact sensor 110 determines whether there is contact with a human body, that is, whether an electrode 120 directly comes in contact with the human body, or whether the electrode 120 comes within a recognizably close distance, thereby making contact with the human body in operation S1200. When the determination result shows that contact is made, the contact sensor 110 outputs a signal indicating that contact is made to a central processing unit such as a microcontroller, and thus instructs the central processing unit to initially operate a suspended operation in operation S1210. Accordingly, when a switch 135 receives the signal output from the central processing unit, if the signal output from the central processing unit indicates signal reception, the switch 135 allows a signal input through the electrode 120 to be passed on to a receiver 131. If the signal output from the central processing unit indicates signal transmission, the switch 135 allows a signal output from a transmitter 133 to be connected to the electrode 120, thereby performing an overall operation in operation S1220.

Figure 2:
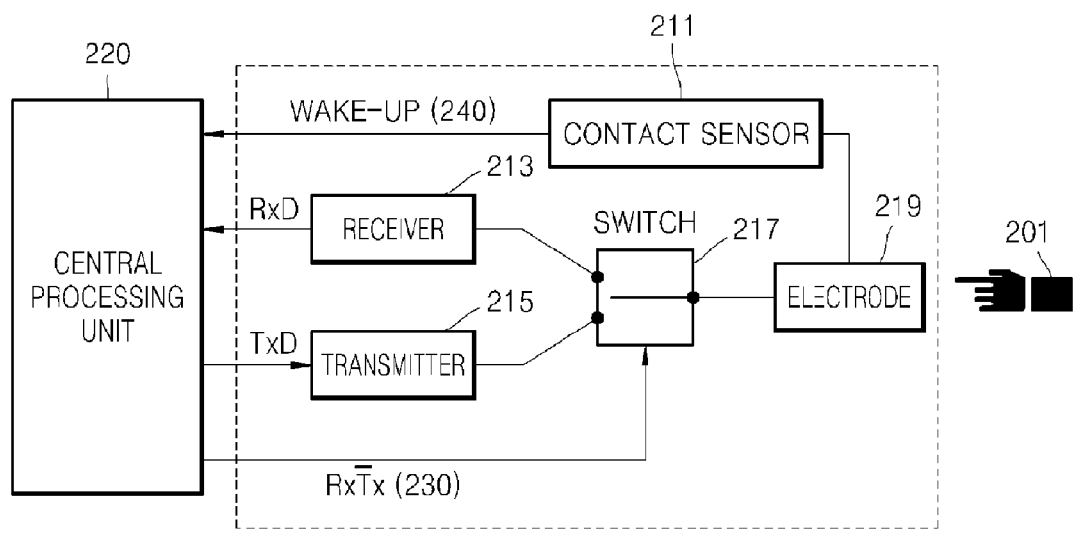
FIG. 2 is a block diagram illustrating a configuration of a time division multiplexing communication apparatus having a human body contact sensor according to an embodiment of the present invention.
Figure 6:
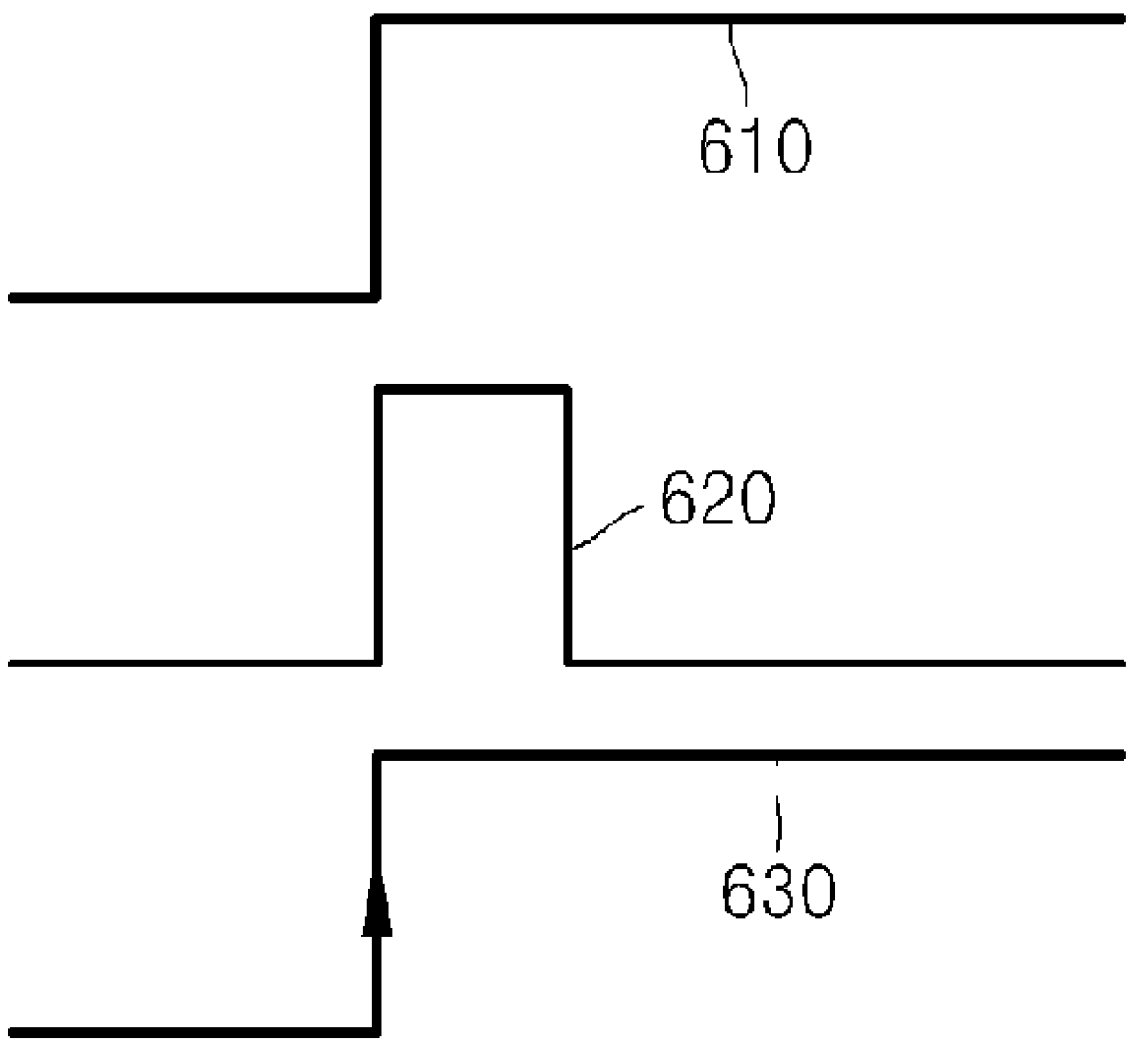
FIG. 6 illustrates an example of an output signal of a contact sensor.

FIG. 2 is a block diagram illustrating a configuration of a time division multiplexing communication apparatus having a human body contact sensor according to an embodiment of the present invention Referring to FIG. 2, when a human body 201 comes in contact with an electrode 219 for a transmitting/receiving operation, a contact sensor 211 detects this, and outputs a wake-up signal 240 to a central processing unit 220. Then, the central processing unit 220, which has been in a sleep mode or has performed another operation except for human body communication, initially performs a receiving operation for the human body communication. When operating in a receiving mode, the central processing unit 220 outputs a signal $Rx\overline{Tx}$ 230 to a switch 217 that completes a transmitting/receiving path, so that an electrical path is formed between the electrode 219 and a receiver 213. The wake-up signal 240 may be continuously output while contact is maintained after initial contact is made, may be output having a constant pulse width at the moment when contact is made, or may be output using a positive or negative trigger method. This is shown in FIG. 6. The central processing unit 220 is set to no longer be under the influence of the wake-up signal 240 once the central processing unit 220 is in the wake-up state. When a sensing operation of the contact sensor 211 is too sensitive, a channel is formed, and a load condition of the electrode 219 changes according to whether the switch 217 for a transmitting/receiving operation is driven. Such change may produce erroneous operations of the contact sensor 211, and thus the wake-up signal 240 of the contact sensor 211 has to be ignored if the wake-up signal 240 is produced after contact is made.

Figure 7:
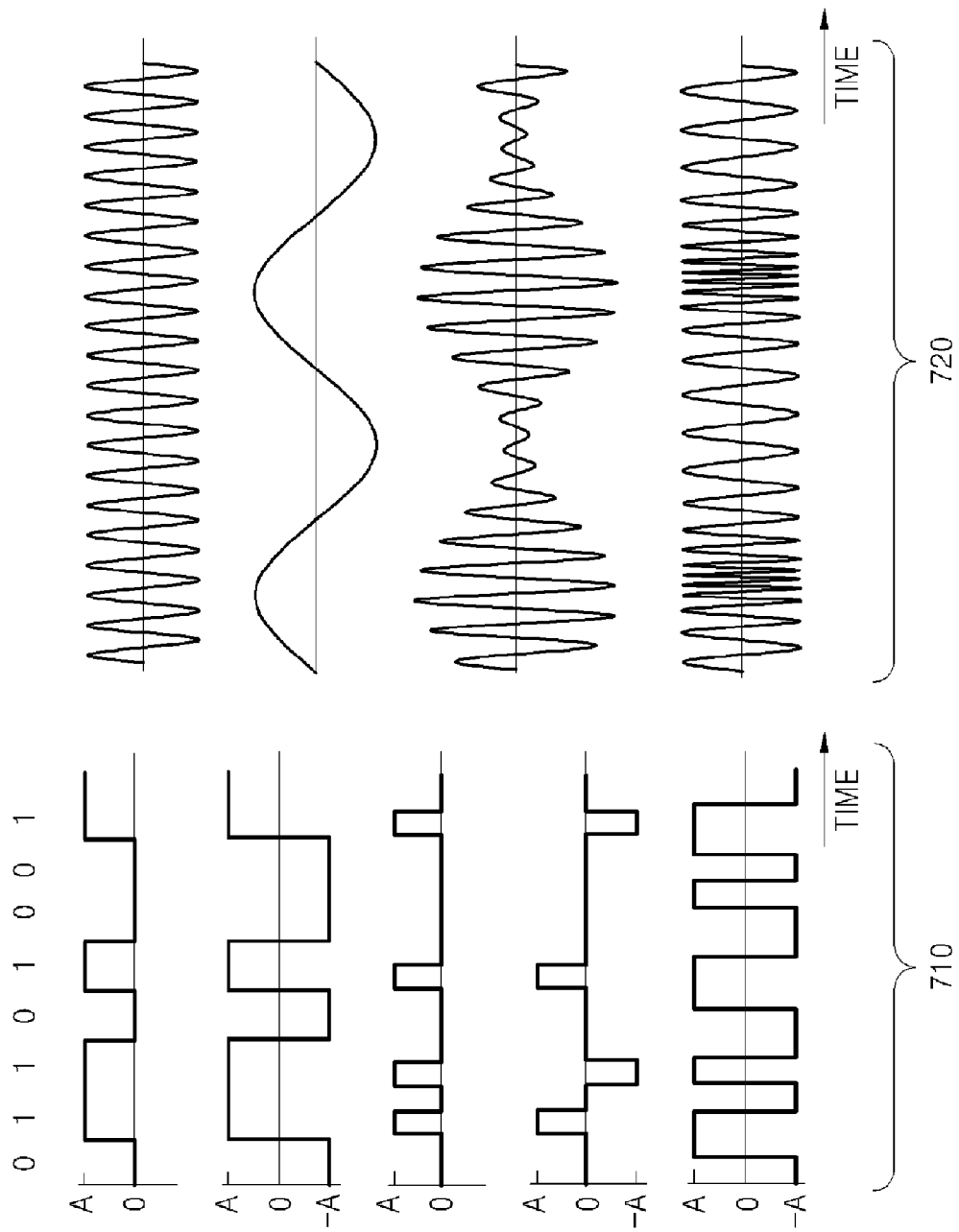
FIG. 7 illustrates examples of a signal that can be communicated through a human body in a communication apparatus having a human body contact sensor according to an embodiment of the present invention.

FIG. 7 illustrates examples of signals that can be communicated by using a communication apparatus according to an embodiment of the present invention. The examples include signals using a pulse modulation method 710 including a Manchester coding and a continuous frequency modulation method 720. In the case of a signal using the pulse modulation method 710, a filter may be used to enhance efficiency of frequency usage and to constraint 'spurious' According to the communication apparatus of the present invention, a digital signal which has not undergone the continuous frequency modulation may be transmitted and received by using a time division multiplexing method. In this case, the receiver 213 is composed of a circuit for restoring a weak input signal into a digital signal, and a transmitter 215 has a circuit for providing an amplifying function for converting a signal received from the central processing unit 220 to be into a continuous frequency signal.

The communication apparatus of FIG. 2 can be used even when the same carrier frequency is used in transmitting and receiving processes. In this case, the receiver 213 has a continuous frequency demodulation means, and the transmitter 215 has a continuous frequency modulation means.

Figure 3:
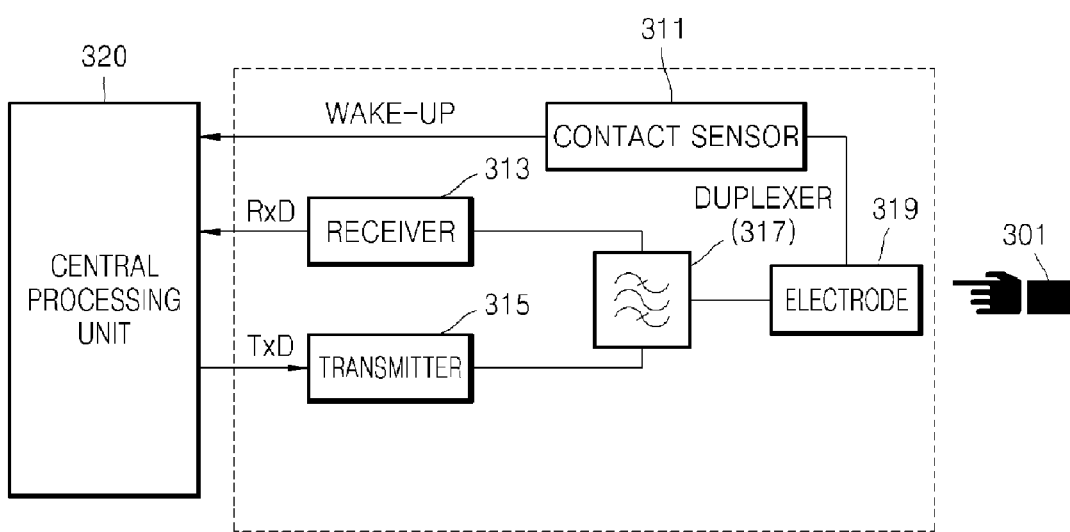
FIG. 3 is a block diagram illustrating a configuration of a frequency division multiplexing communication apparatus having a human body contact sensor according to an embodiment of the present invention.

FIG. 3 is a block diagram illustrating a configuration of a frequency division multiplexing communication apparatus having a human body contact sensor according to an embodiment of the present invention.

FIG. 3 illustrates a configuration of a communication apparatus according to an embodiment of the present invention where different carrier frequencies are used in transmission and reception processes. Since different carrier frequencies are used in transmission and reception processes, a duplexer 317 is used to distinguish paths of input and output signals. By using a continuous frequency demodulation circuit, a receiver 313 restores a signal received through a human body 301 into a digital signal RxD, and outputs the restored digital signal RxD to a central processing unit 320. A transmitter 315 modulates a digital signal TxD received from the central processing unit 320 in continuous frequency modulation method by using a carrier frequency, and outputs the modulated digital signal TxD to the human body 301 via the duplexer 317 and an electrode 319. In this case, unlike in the case of FIG. 2, a selection signal from the central processing unit 320 is not necessary.

Figure 4:
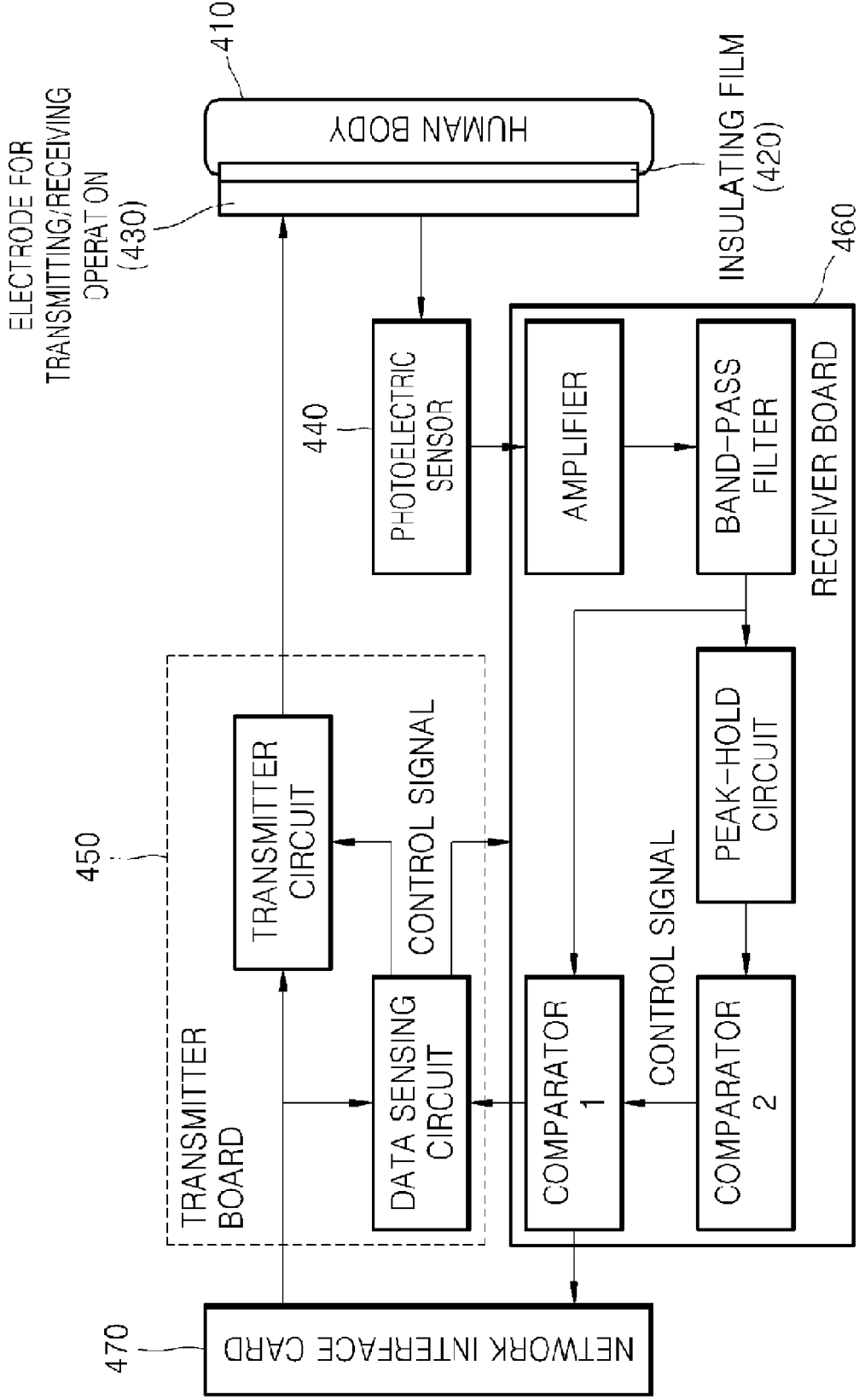
FIG. 4 is a block diagram illustrating a configuration of a communication apparatus using a conventional photoelectric sensor.

FIG. 4 is a block diagram illustrating a configuration of a communication apparatus using a conventional photoelectric sensor. FIG. 4 illustrates a transmitter/receiver circuit using a method capable of detecting an electric field induced to a human body even in a non-contact state by using a conventional photoelectric effect. In this method, a weak electric field input to an electrode 430 for a transmitting/receiving operation when in contact with a human body 410 is formed into an electric signal via a photoelectric sensor 440. An insulating film 420 is attached on a side where the electrode 430 for a transmitting/receiving operation is in contact with the human body 410. A signal received from the photoelectric sensor 440 is transmitted to a network interface card 470 via a receiver 460. A signal receiving from the network interface card 470 is transmitted to the human body 410 via a transmitter 450. The functions of the transmitter 450 and the receiver 460 can be understood by those skilled in the art, and thus detailed descriptions thereof will be omitted.

Meanwhile, in this case, more power is consumed even if data transmission is implemented to be faster than that in the method used in FIGS. 2 and 3.

Figure 5:
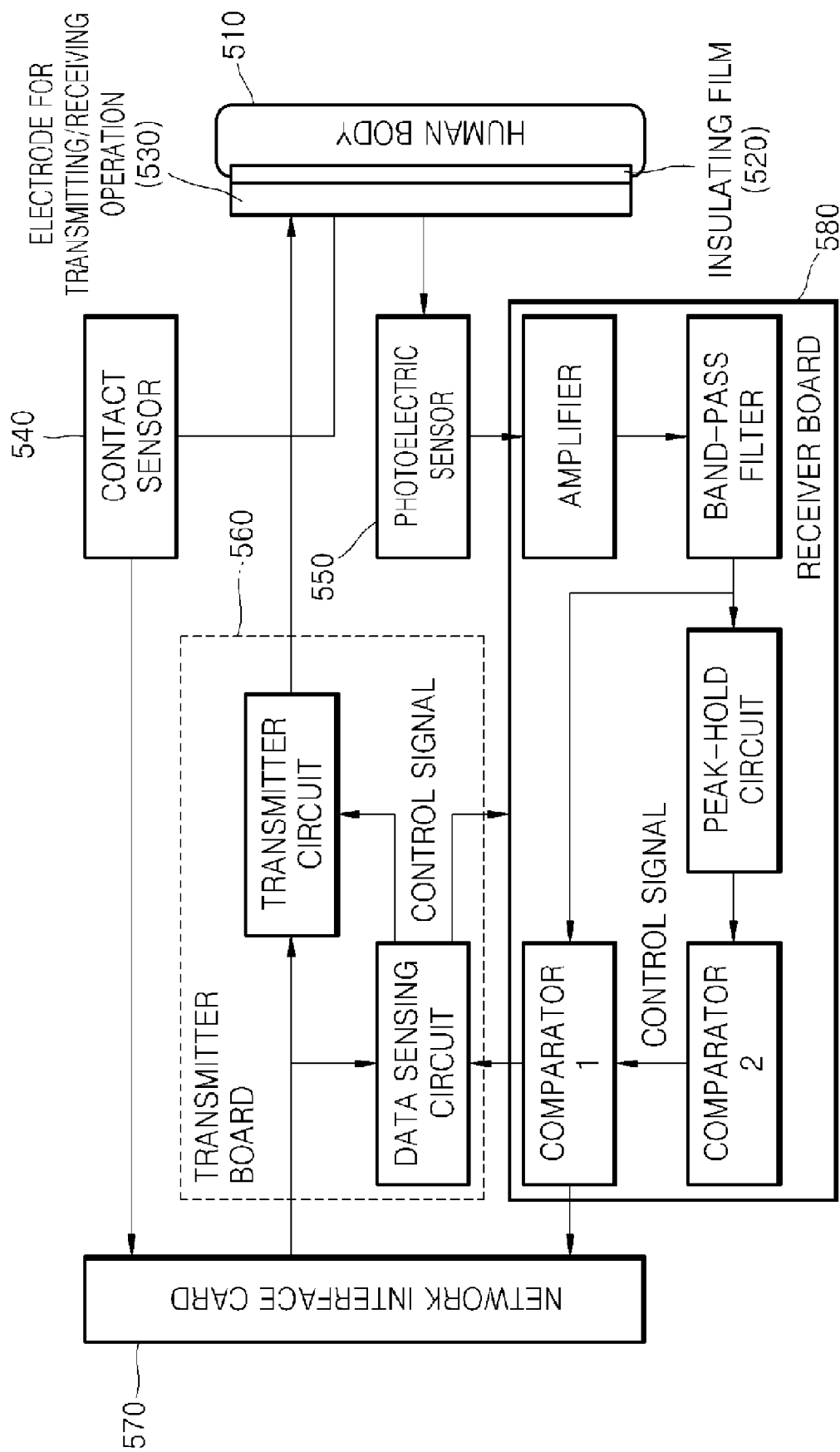
FIG. 5 is a block diagram illustrating a configuration of a communication apparatus using a photoelectric sensor having a contact sensor according to an embodiment of the present invention.

Therefore, a communication apparatus of FIG. 5 according to another embodiment of the present invention has a configuration in which a contact sensor 540 is additionally provided to significantly improve on the conventional method shown in FIG. 4. The contact sensor 540 uses a conductive contact pad connected to an electrode 530 for a transmitting/receiving operation, and thus whether the contact pad approaches to a human body 510 in a non-contact state is determined even when contact is not made, so as to reduce power consumption by not using a photoelectric sensor 550, a transmitter 560, and a receiver 580 which consume a lot of power until contact is made. The functions of the transmitter 560 and the receiver 580 can be understood by those skilled in the art, and thus detailed descriptions thereof will be omitted.

Figure 8:
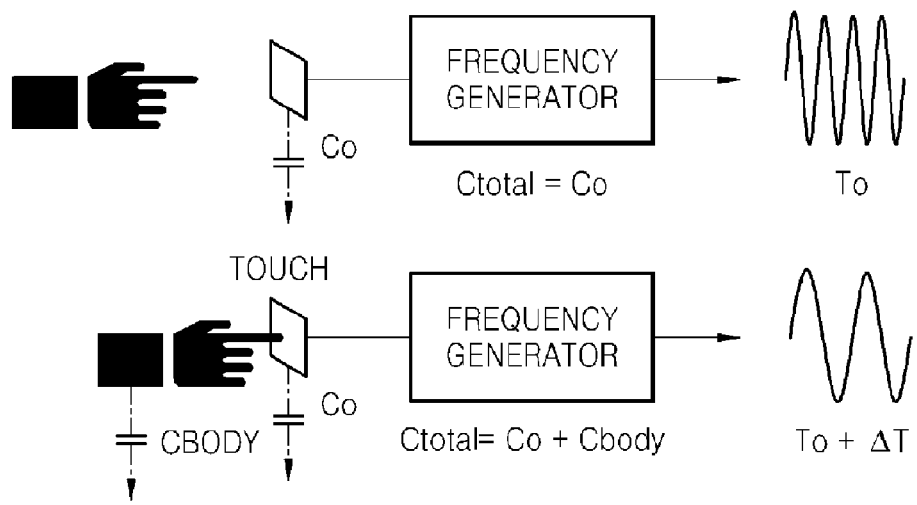
FIG. 8 illustrates an operating principle of a conventional capacitive contact sensor.
Figure 9:
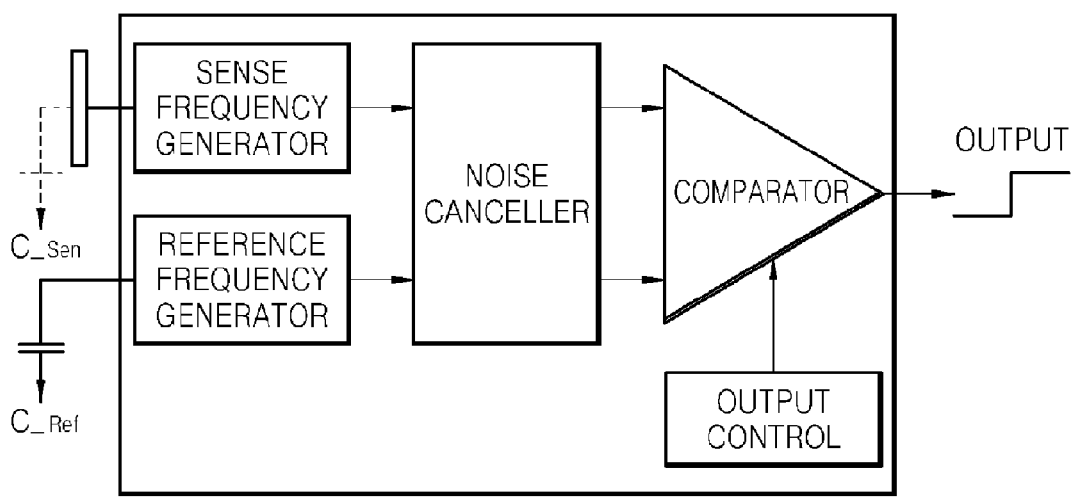
FIG. 9 is a block diagram illustrating a configuration of a conventional capacitive contact sensor.

FIG. 8 illustrates an operating principle of a contact sensor. When there is no human body contact, a natural oscillating frequency based on a reference capacitance is generated. When there is human body contact, a load capacitance changes, and thus, a change in an oscillating frequency is produced so that an output signal is generated via a comparator. This circuit configuration is shown in FIG. 9. The operating principle of the contact sensor is also understood by those skilled in the art, and thus detailed descriptions thereof will be omitted.

Figure 10:
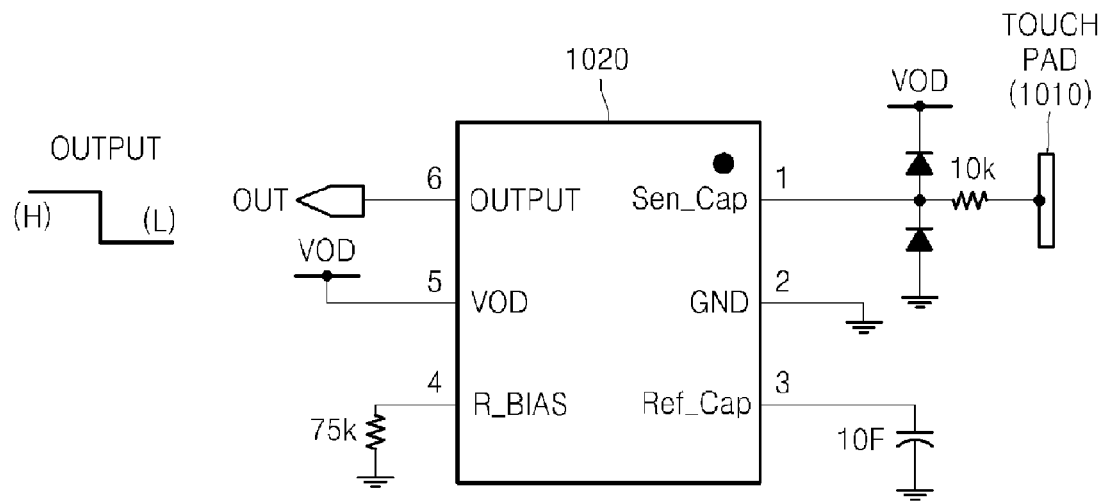
FIG. 10 illustrates a conductive pad (electrode) using a contact sensor according to an embodiment of the present invention.
Figure 11:
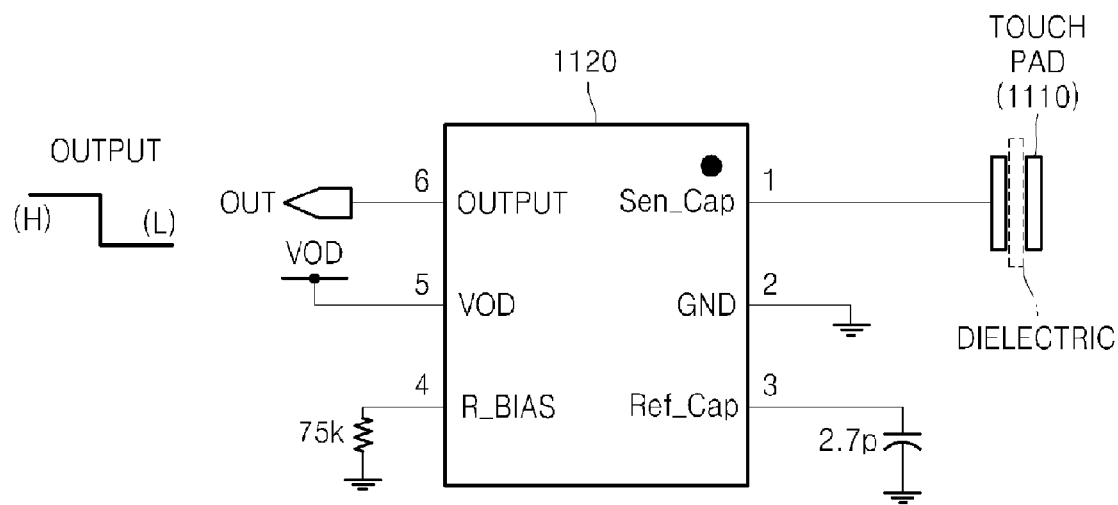
FIG. 11 illustrates a conductive pad (electrode) using a contact sensor when in a non-contact state according to an embodiment of the present invention.

FIG. 10 illustrates a case of using a single channel contact sensor 1020 employing a conductive contact pad 1010 according to an embodiment of the present invention. FIG. 11 illustrates a case of using a single channel contact sensor 1120 employing a conductive non-contact pad 1110 according to an embodiment of the present invention. The single channel contact sensor 1120 can be used in the communication apparatus having the non-contact electrode for a transmitting/receiving operation of FIG. 5. Although the electrode (a contact pad) for a transmitting/receiving operation is constructed to be a signal channel in the present embodiment, if the electrode for a transmitting/receiving operation is constructed in plural in order to maintain a stable contact with a human body, a multi-channel sensor may be used.

When a contact sensor is used, contact sensitivity can be controlled by controlling a reference capacitance. When a sensor that is set to have high contact sensitivity is used, it is possible to detect a human body approaching a distance of a few mm to cm within a contact pad (or an electrode). In this case, by controlling a time required for a micro processing unit to reach a normal state from a stand-by state and a time for a transmitter/receiver circuit to reach a normal state, it is possible to prepare to form a channel at the same time when contact is made.

The circuit constituting a contact sensor that can be used in the present invention can use not only a conductive contact sensor but also a sensor that can sense pressure and other human contact.

The aforementioned micro-controller may be embedded into a communication apparatus. However, a function of a micro processing unit for in a possible human communication device, such as a mobile phone, a personal digital assistant (PDA), an MP3, a portable video information device, a personal computer (PC), a notebook computer, a printer, etc, may be included in the corresponding device.

The communication apparatus having human body contact sensing function according to the present invention may be used when communication is achieved between portable devices, between a portable device and a fixed device, and between fixed devices through a human body as a communication medium.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion.

While the present invention has been particularly shown and described with reference to exemplary embodiments thereof, it will be understood by those skilled in the art that various changes in form and details may be made therein without departing from the spirit and scope of the present invention as defined by the appended claims.

The invention claimed is:

1. A communication apparatus having a human body contact sensing function wherein the communication apparatus performs communication in contact with a central processing unit and a human body, the communication apparatus comprising:
    an electrode that comes in contact with the human body;
    a contact sensor configured to connect to the electrode, and instruct the central processing unit to perform an initial operation if contact with the human body is sensed; and
    a data processing unit configured to receive a control signal from the central processing unit so as to select whether to transmit or receive data, and perform a transmitting or receiving operation according to the control signal,
    wherein the data processing unit is configured to perform transmitting and receiving of the data by using a time-division method,
    wherein the data processing unit comprises:
        a first receiver configured to restore a base-band signal received through the human body into an original digital signal,
        a first transmitter configured to output a signal received from the central processing unit to the human body as a base-band signal, and
        a first switch that is connected to the transmitter and the receiver, and is configured to select whether to transmit or receive the data to/from the human body in response to the control signal.

2. The communication apparatus of claim 1, wherein the contact sensor instructs the central processing unit to perform the initial operation by sensing direct contact between the human body and the electrode or by sensing approach of the human body.

3. The communication apparatus of claim 2, wherein the contact sensor instructs the central processing unit to perform the initial operation by generating a signal having a constant value while the contact is maintained, by generating a signal having pulses of a constant width from the moment when the contact is made, or by generating a signal using a positive or negative trigger method.

4. The communication apparatus of claim 1, wherein the base-band signal includes an ultra wide band (UWB) signal which has undergone spreading and channel coding based on a communication channel feature, and has a significantly short pulse period.

5. A communication apparatus having a human body contact sensing function wherein the communication apparatus performs communication in contact with a central processing unit and a human body, the communication apparatus comprising:
    an electrode that comes in contact with the human body;
    a contact sensor configured to connect to the electrode, and instruct the central processing unit to perform an initial operation if contact with the human body is sensed; and
    a data processing unit configured to receive a control signal from the central processing unit so as to select whether to transmit or receive data, and perform a transmitting or receiving operation according to the control signal,
    wherein the data processing unit uses a continuous frequency modulation method in which the same carrier frequency is used when data is transmitted and received,
    wherein the data processing unit comprises:
        a second receiver configured to restore a signal received through the human body into a digital signal by using a continuous frequency demodulation method,
        a second transmitter configured to modulate a digital signal received from the central processing unit into a continuous frequency signal by using a continuous frequency modulation method, and output the continuous frequency modulated signal to the human body, and
        a second switch that is connected to the transmitter and the receiver, and is configured to select whether to transmit or receive the data to/from the human body in response to the control signal.

6. The communication apparatus of claim 5, wherein a transmission carrier frequency is different from a reception carrier frequency.

7. The communication apparatus of claim 6, wherein the data processing unit further comprises:
    a third receiver configured to restore a signal received through the human body by using a continuous frequency demodulation method into a digital signal;
    a third transmitter configured to modulate a digital signal received from the central processing unit into a continuous frequency signal by using a continuous frequency modulation method, and outputs the continuous frequency modulated signal to the human body; and
    a duplex configured to distinguish paths for the transmission signal and the reception signal which have undergone the continuous frequency modulation.

8. The communication apparatus of claim 1, wherein the contact sensor comprises a multi-channel sensor if the electrode is provided in plural.

9. The communication apparatus according to claim 1, further comprising:
    a sensor that converts an electric field input through the electrode into an electric signal,
    wherein the data processing unit is configured to restore the electric signal into original data to be transmitted to an external device, and convert data received from the external device to output the received data to the electrode, and wherein the contact sensor is configured to generate and output a sensing signal used to detect whether contact is made with the human body and indicate the result of detection so that the external device can recognize the result, the contact sensor comprising a multi-channel sensor when the electrode is provided in plural.

10. The communication apparatus of claim 9, wherein the external device performs an initial operation in response to the sensing signal.

11. The communication apparatus of claim 9, wherein the contact sensor generates the sensing signal by sensing direct contact with the human body or by sensing approach of the human body.

* * * * *